United States Patent [19]

Miura et al.

[11] Patent Number: 5,959,088
[45] Date of Patent: Sep. 28, 1999

[54] PROCESS FOR PRODUCING ERYTHROMYCIN DERIVATIVES

[75] Inventors: Yutaka Miura, Tokyo; Kazuhiro Oishi, Shizuoka-ken; Yasushige Kawasaki, Tokyo, all of Japan

[73] Assignee: Chugai Seiyaku Kabushiki Kaisha, Tokyo, Japan

[21] Appl. No.: 09/011,142

[22] PCT Filed: Aug. 5, 1996

[86] PCT No.: PCT/JP96/02191

§ 371 Date: Apr. 9, 1998

§ 102(e) Date: Apr. 9, 1998

[87] PCT Pub. No.: WO97/06177

PCT Pub. Date: Feb. 20, 1997

[30] Foreign Application Priority Data

Aug. 3, 1995 [JP] Japan ..................... 7-229598

[51] Int. Cl.⁶ ............... C07H 1/00; C07H 17/08
[52] U.S. Cl. ............................. 536/7.2; 536/18.5
[58] Field of Search ............... 536/7.2, 7.5, 18.5

[56] References Cited

U.S. PATENT DOCUMENTS 4,672,056  6/1987  Fernandes et al. .................. 514/29
5,008,249  4/1991  Omura et al. ...................... 514/29

*Primary Examiner*—Elli Peselev
*Attorney, Agent, or Firm*—Browdy and Neimark

[57] ABSTRACT

A process for the preparation of fumaric acid salts of compounds of general formula (II) (wherein $R_1$ is lower alkyl; and $R_2$ is lower alkyl), is characterized by reacting a compound, which is prepared from erythromycin A through acetylation of the hydroxyl at position 2', formulation and hemiketalization of the hydroxyl at position 4", oxidation of the hydroxyl at position 11, alkylation of the hydroxyl at position 12 and removal of the acetyl at position 2' and the formyl at position 4", with benzyloxycarbonyl chloride under basic conditions, freeing the obtained compound from the benzyloxycarbonyl group thus introduced, alkylating the nitrogen atom at position 3', converting the obtained compound into a fumaric acid salt, recrystallizing the obtained crude salt from an alcoholic solvent, and recrystallizing the obtained crystal from hydrous ethyl acetate again.

15 Claims, 7 Drawing Sheets

PROCESS FOR PRODUCING ERYTHROMYCIN DERIVATIVES

TECHNICAL FIELD

This invention relates to a process for producing erythromycin derivatives and fumarate crystals of erythromycin derivatives produced by the process.

BACKGROUND ART

Compounds represented by the general formula (II):

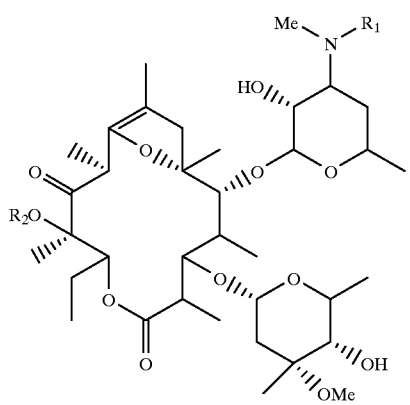

(II)

(where $R_1$ is a lower alkyl group and $R_2$ is a lower alkyl group) are described in Japanese Patent Public Disclosure No. 56873/1994, etc. and are known to have a capability for promoting the movement of digestive tracts.

Process for producing these compounds are described in Japanese Patent Public Disclosure No. 56873/1994, Bioorg. & Med. Chem. Lett., Vol. 4, No. 11, p. 1347, 1994, etc.

However, the processes described in these references have several drawbacks that make them unsuitable for commercial operations, such as the multitude of the steps involved, much use of column chromatography for purification and the use of reagents (e.g., iodine) that are unsuitable for large-scale production. Further, the compounds are required to have high quality in such terms as stability, uniformity and compliance with standards if they are to be used for supplying pharmaceuticals or starting materials therefor of the kind that is to be produced by the process of the invention.

DISCLOSURE OF INVENTION

The present inventors conducted intensive studies in order to deal with this situation and found an efficient process for producing and purifying fumarates of compounds represented by the general formula (II):

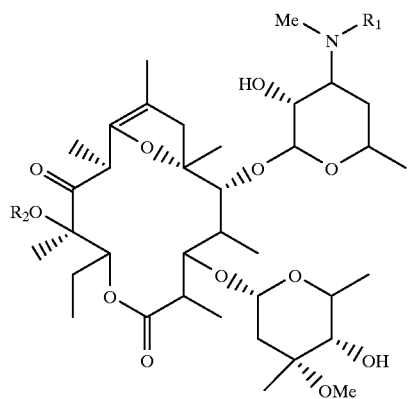

(II)

(where $R_1$ is a lower alkyl group and $R_2$ is a lower alkyl group); the inventors also found that the fumarate crystals purified by the process had better quality as pharmaceuticals or starting materials therefor than the heretofore obtained crystals. The present invention has been accomplished on the basis of these findings.

Thus, the present invention relates to a process for producing a fumarate of a compound of the general formula (II):

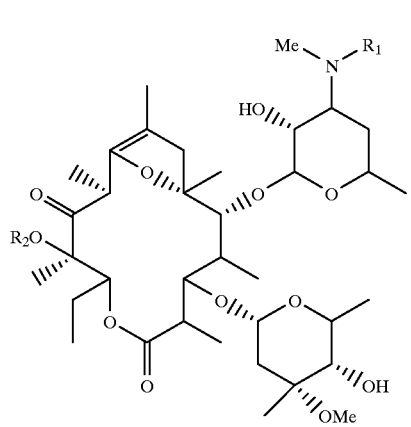

(II)

(where $R_1$ is a lower alkyl group and $R_2$ is a lower alkyl group) from erythromycin A [formula (I)]:

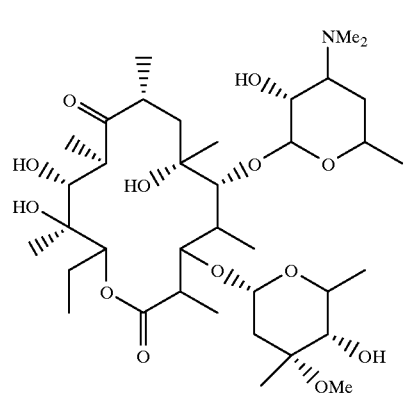

(I)

comprising the steps of acetylating the hydroxyl group in position 2' of erythromycin A, formylating the hydroxyl group in position 4" and thereafter performing a reaction for the formation of hemiketal, thereby producing a compound of the formula (III):

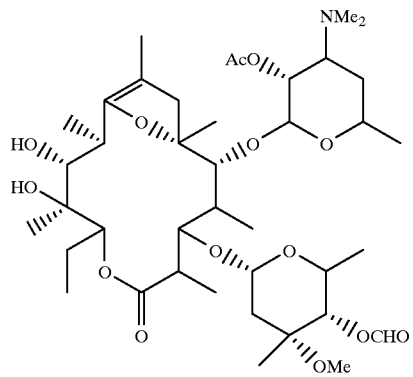

oxidizing the hydroxyl group in position 11 of the compound (III) to produce a compound of the formula (IV):

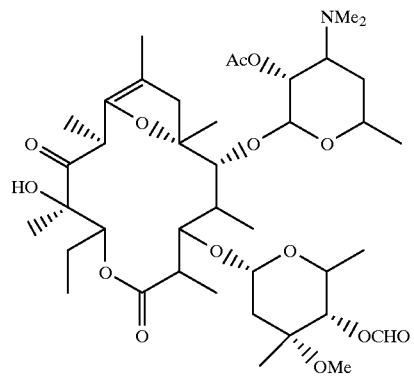

alkylating the hydroxyl group in position 12 of the compound (IV), removing the acetyl group in position 2' and the formyl group in position 4" to produce a compound of the general formula (V):

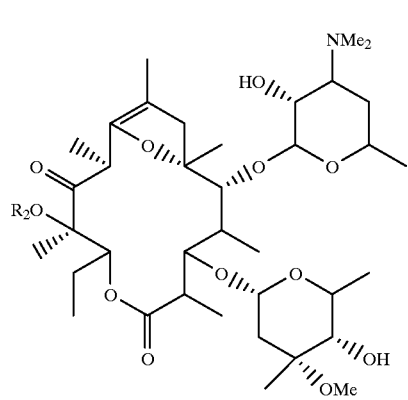

(where $R_2$ is a lower alkyl group), reacting the compound (V) with benzyloxycarbonyl chloride under basic conditions, thereafter removing the introduced benzyloxycarbonyl group, subsequently alkylating the nitrogen atom in position 3', thereafter converting the compound to a fumarate in a crude crystal form, then recrystallizing the crude crystal from an alcoholic solvent and thereafter effecting another recrystallization from hydrous ethyl acetate.

The invention also relates to a process for producing a fumarate of a compound of the general formula (II):

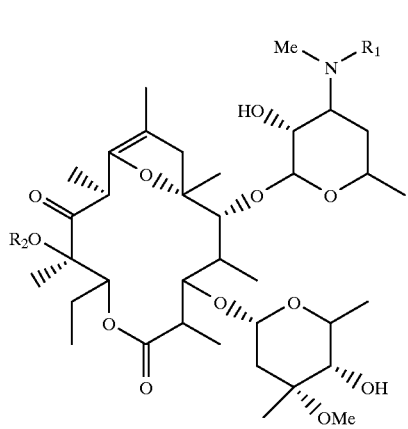

(where $R_1$ is a lower alkyl group and $R_2$ is a lower alkyl group) from erythromycin A [formula (I)]:

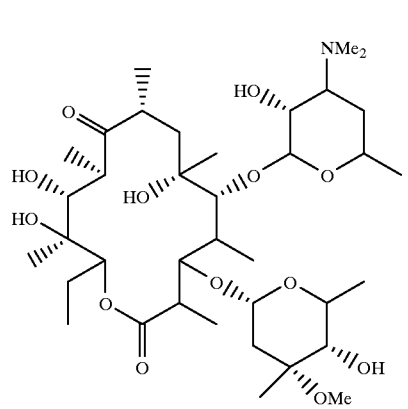

comprising the steps of acetylating the hydroxyl group in position 2' of erythromycin A, formylating the hydroxyl group in position 4" and thereafter performing a reaction for the formation of hemiketal, thereby producing a compound of the formula (III):

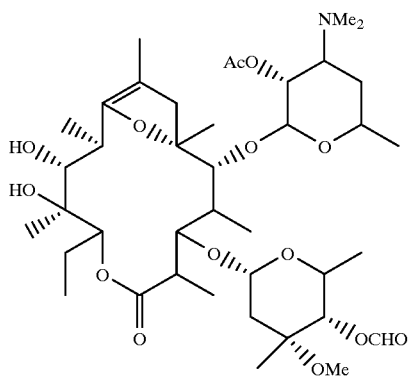

oxidizing the hydroxyl group in position 11 of the compound (III) to produce a compound of the formula (IV):

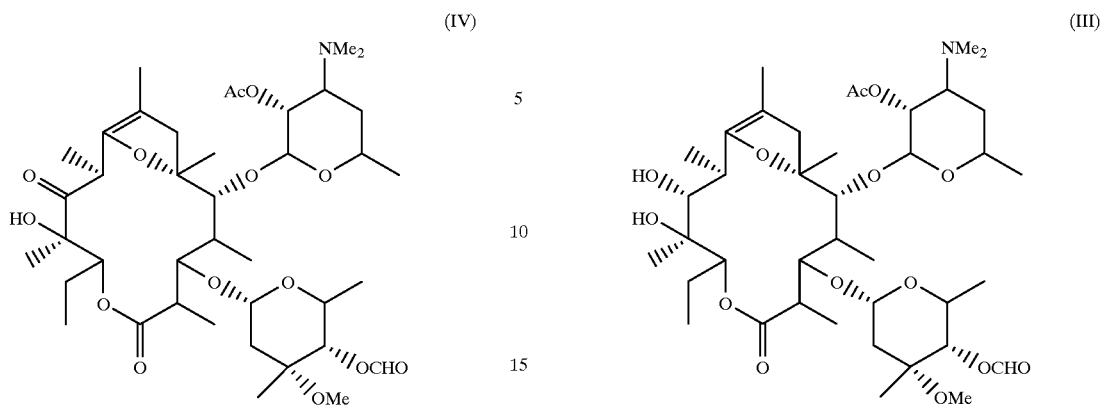

alkylating the hydroxyl group in position 12 of the compound (IV), removing the acetyl group in position 2' and the formyl group in position 4" to produce a compound of the general formula (V):

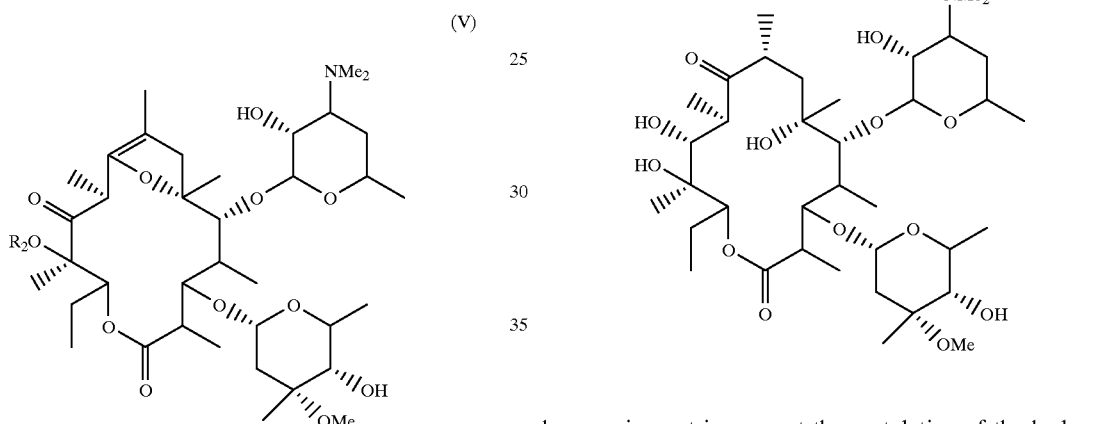

(where $R_2$ is a lower alkyl group), reacting the compound (V) with benzyloxycarbonyl chloride under basic conditions, thereafter removing the introduced benzyloxycarbonyl group, subsequently alkylating the nitrogen atom in position 3', and thereafter converting the compound to a fumarate.

Among the reactions described above, the acetylation of the hydroxyl group in position 2' of erythromycin A, the formylation of the hydroxyl group in position 4" and the reaction for the formation of hemiketal are preferably carried out in one pot. The term "one pot" as used in the present invention means that the reactions of interest are carried out in one step without isolating and purifying the product of reaction at each stage.

The reaction for alkylating the hydroxyl group in position 12 and the reaction for removing the acetyl group in position 2' and the formyl group in position 4" are also preferably carried out in one pot.

In a particular preferred case, the acetylation of the hydroxyl group in position 2' of erythromycin A and the formylation of the hydroxyl group in position 4" and the reaction for the formation of hemiketal are carried out in one pot and, in addition, the reaction for alkylating the hydroxyl group in position 12 and the reaction for removing the acetyl group in position 2' and the formyl group in position 4" are also carried out in one pot.

In another aspect, the present invention relates to a process for producing a compound of the formula (III):

from erythromycin A of the formula (I):

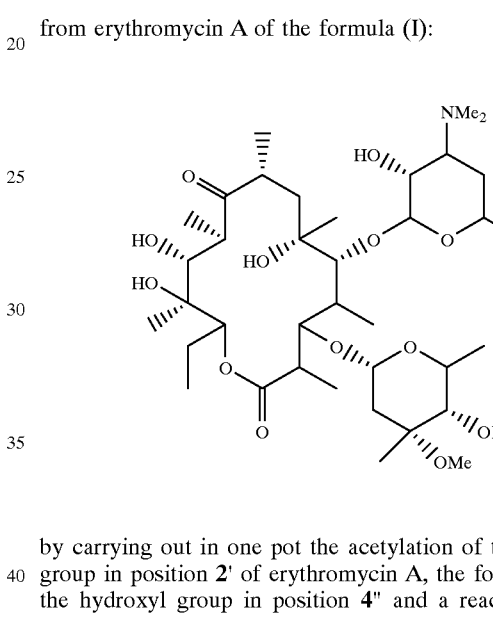

by carrying out in one pot the acetylation of the hydroxyl group in position 2' of erythromycin A, the formulation of the hydroxyl group in position 4" and a reaction for the formation of hemiketal.

The present invention also relates to a process for producing a compound of the general formula (VI):

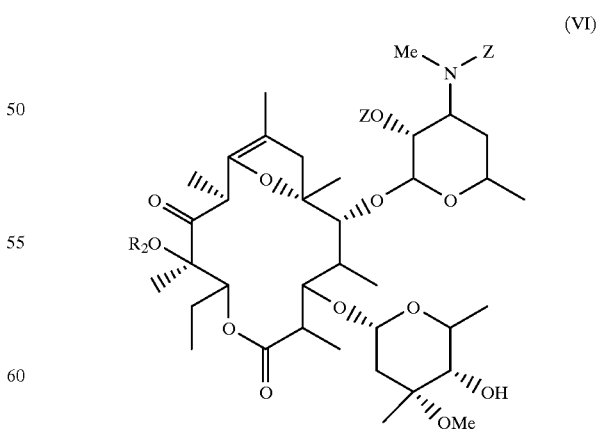

(where $R_2$ is a lower alkyl group and Z is a benzyloxycarbonyl group) by reacting a compound of the general formula (V):

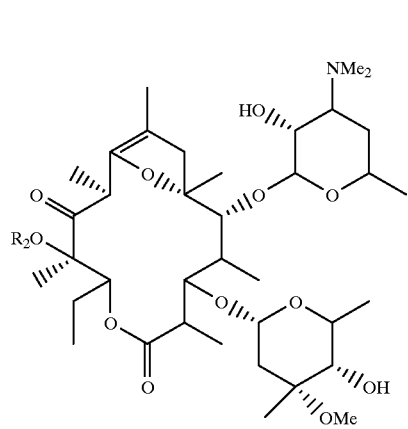

(V)

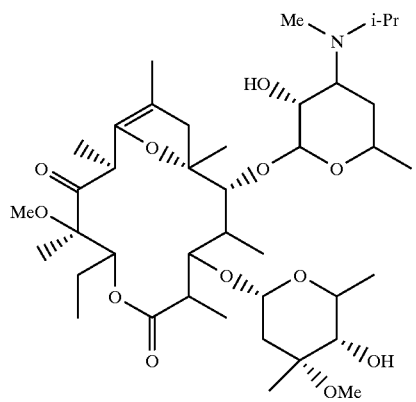

(VII)

(where $R_2$ is a lower alkyl group) with benzyloxycarbonyl chloride under basic conditions.

The present invention also relates to a method of purifying a fumarate of a compound of the general formula (II):

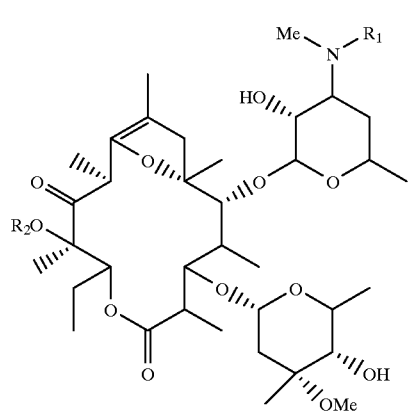

(II)

(where $R_1$ is a lower alkyl group and $R_2$ is a lower alkyl group) by recrystallizing a crude crystal of a fumarate of a compound of the general formula (II):

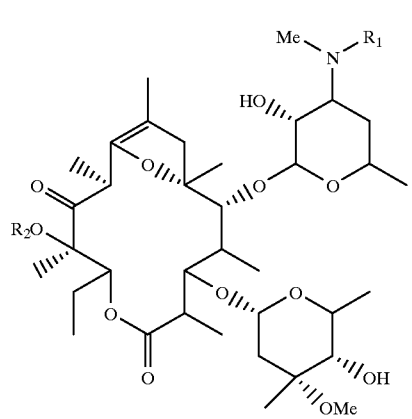

(II)

(where $R_2$, is a lower alkyl group and $R_2$ is a lower alkyl group) from an alcoholic solvent and performing another recrystallization from hydrous ethyl acetate.

In a further aspect, the present invention relates to a fumarate crystal of a compound of the formula (VII):

in which the molar ratio of the compound (VII) to fumaric acid is 2:1 and which is obtained by recrystallization from hydrous ethyl acetate.

BEST MODE FOR CARRYING OUT THE INVENTION

Figure 1:
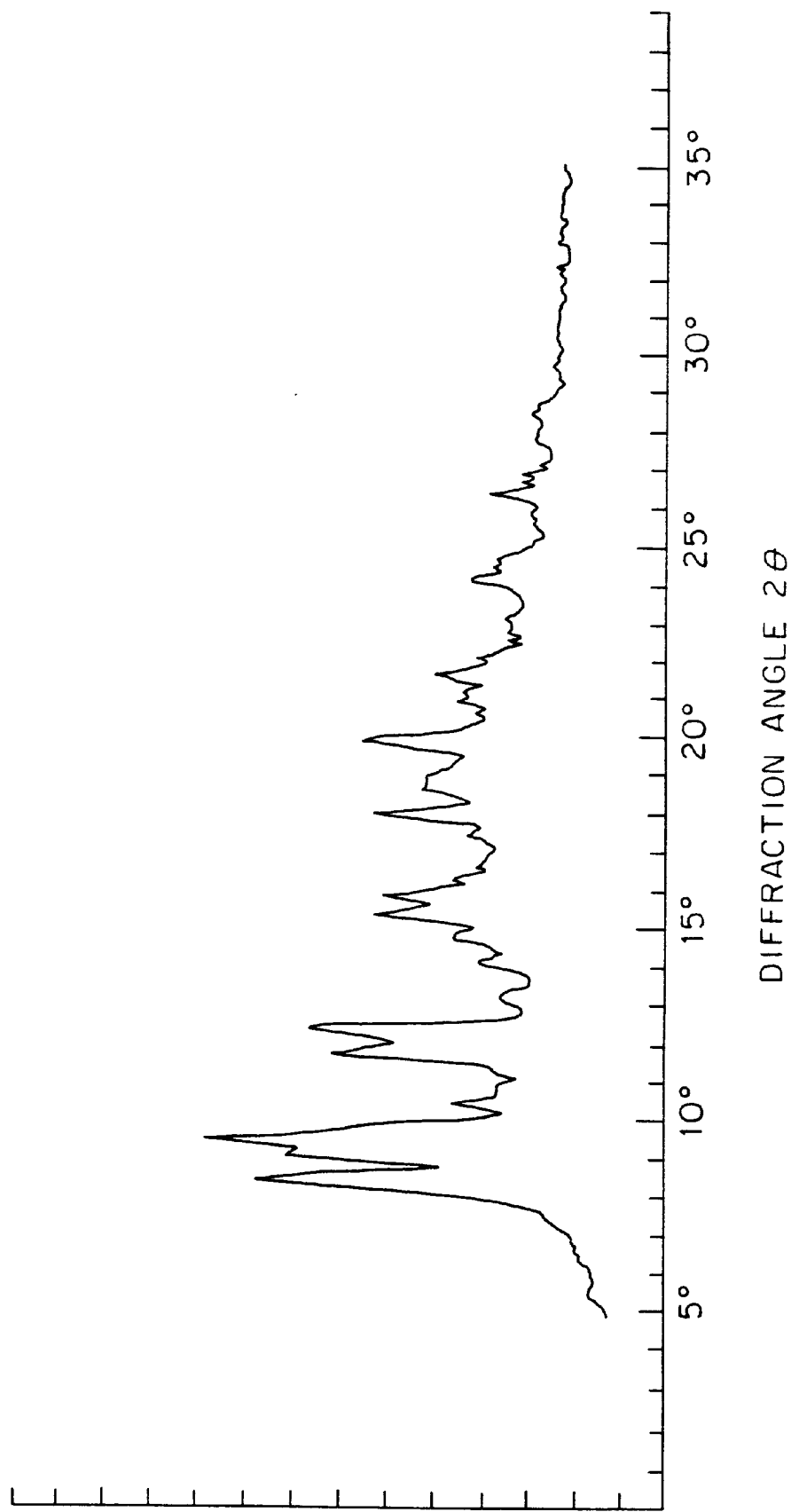
FIG. 1 shows a powder X-ray diffractometer scan for crystal form A.
Figure 2:
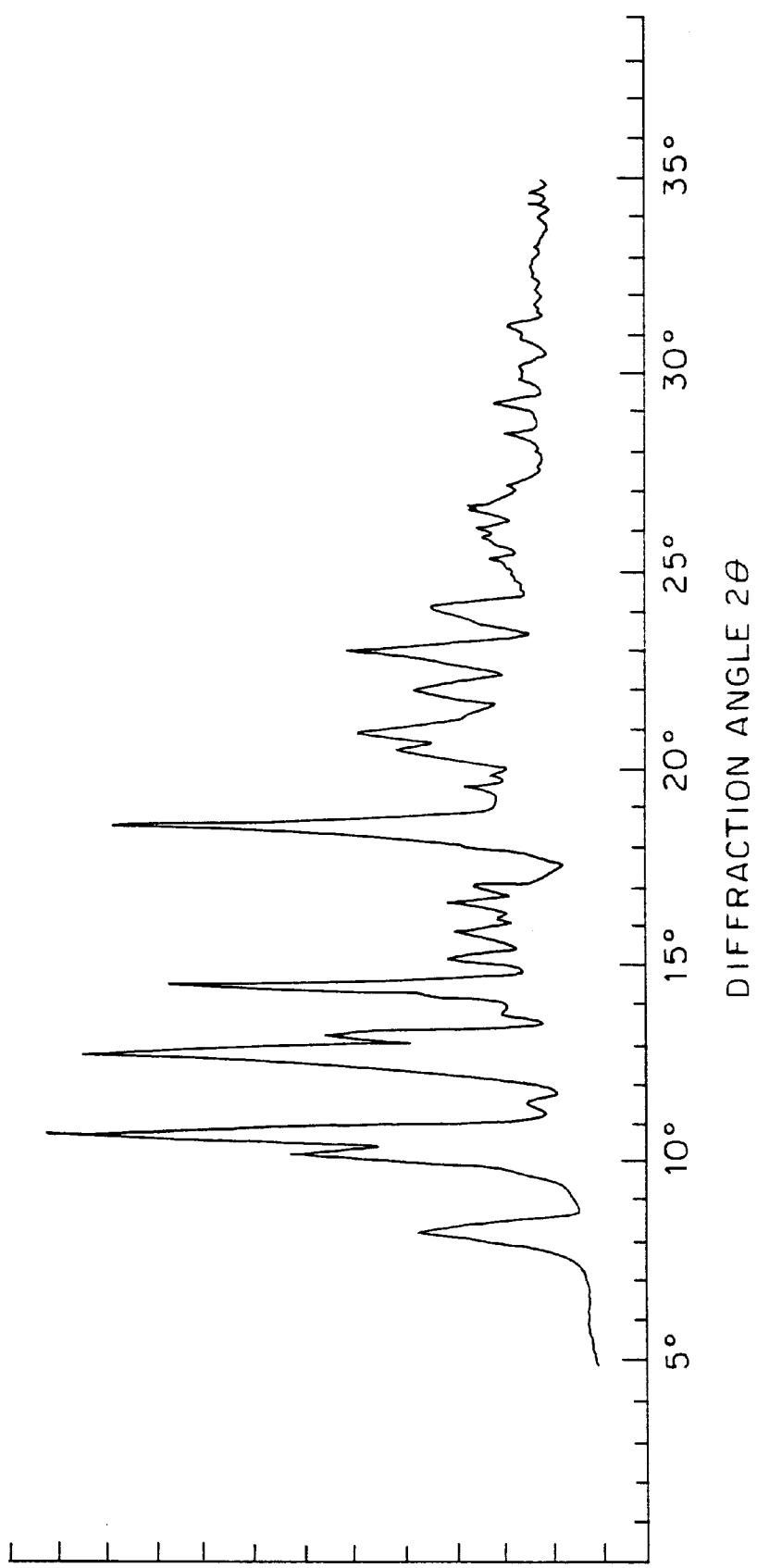
FIG. 2 shows a powder X-ray diffractometer scan for crystal form B.
Figure 3:
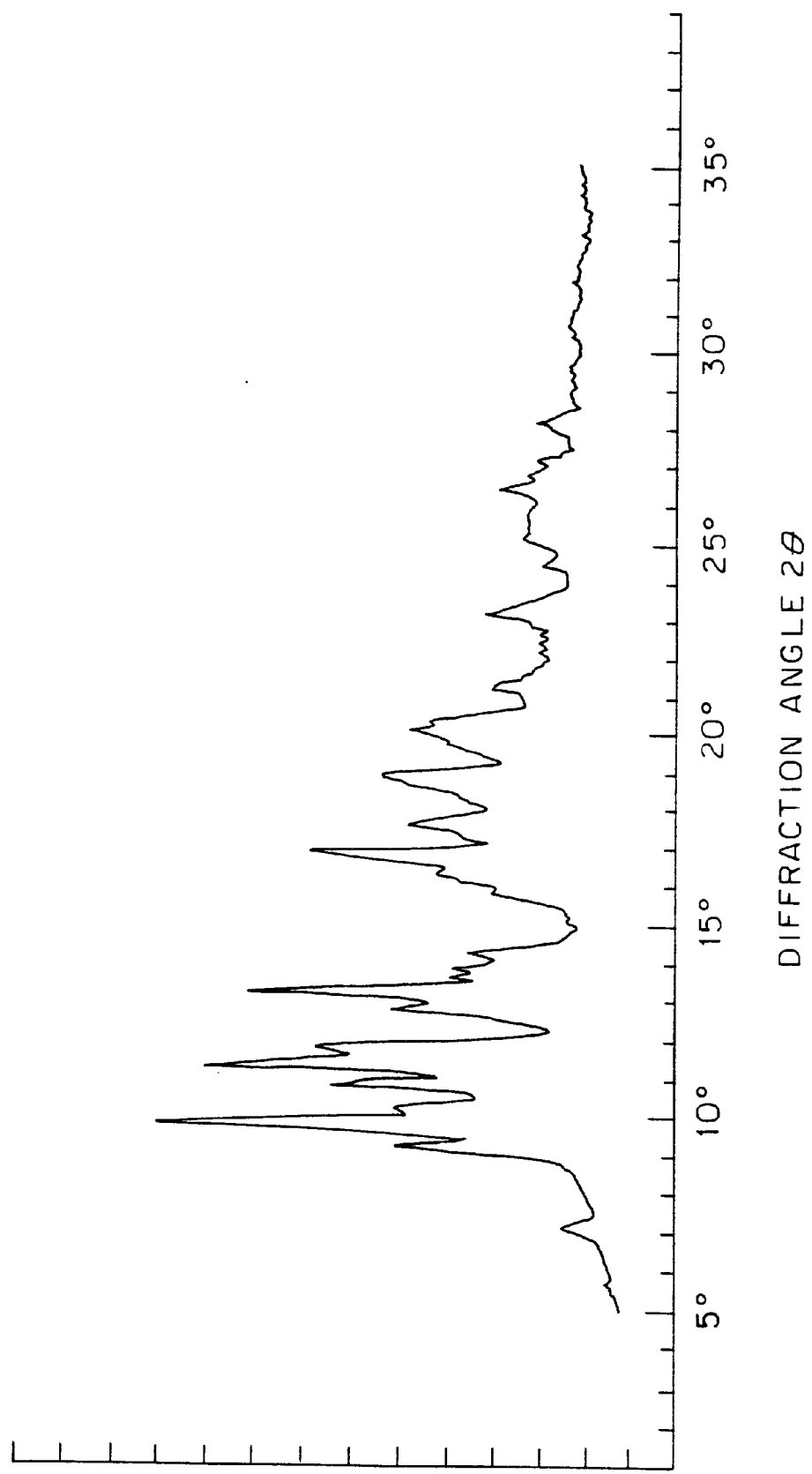
FIG. 3 shows a powder X-ray diffractometer scan for crystal form C.
Figure 4:
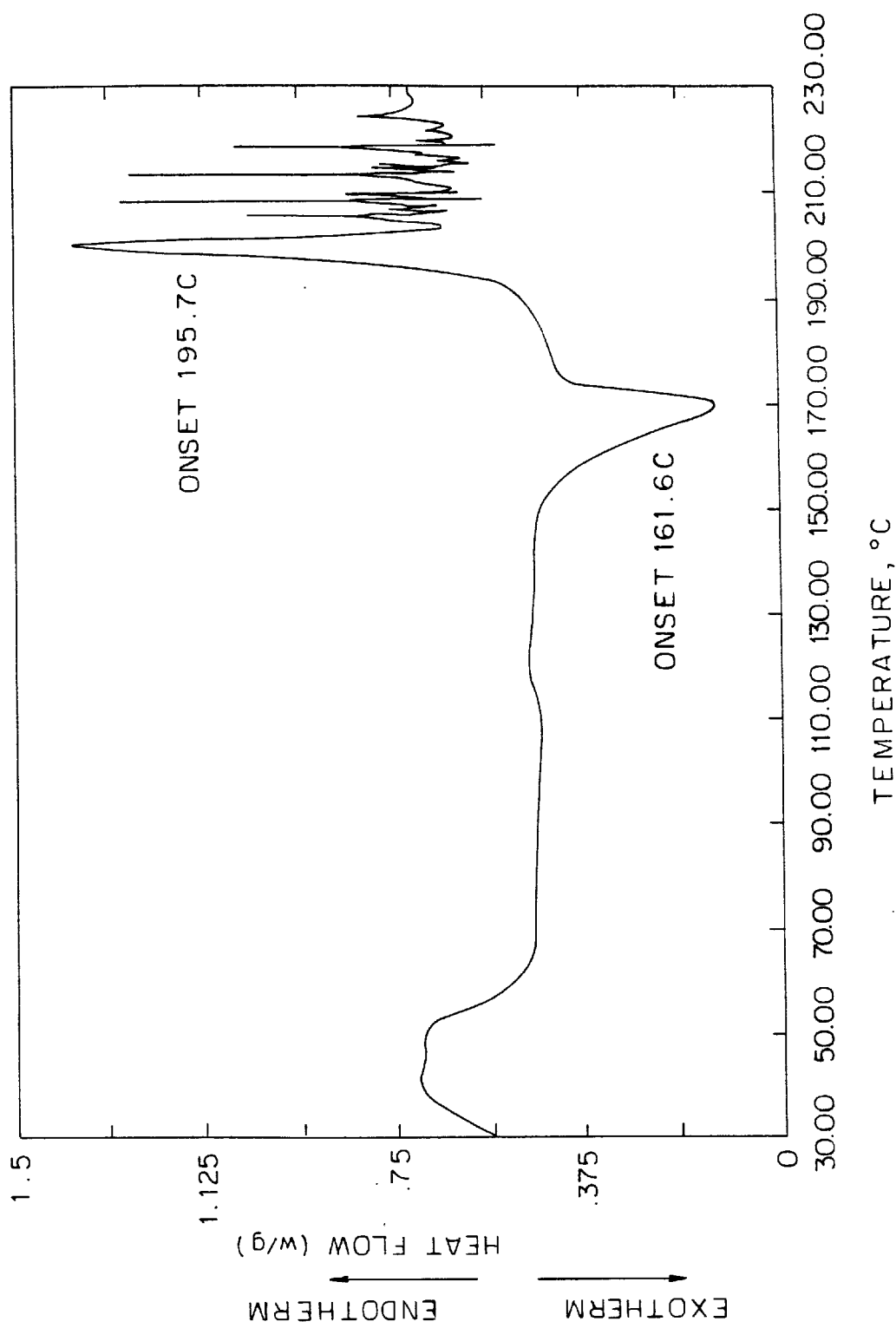
FIG. 4 shows a DSC curve obtained by thermal analysis of crystal form A.
Figure 5:
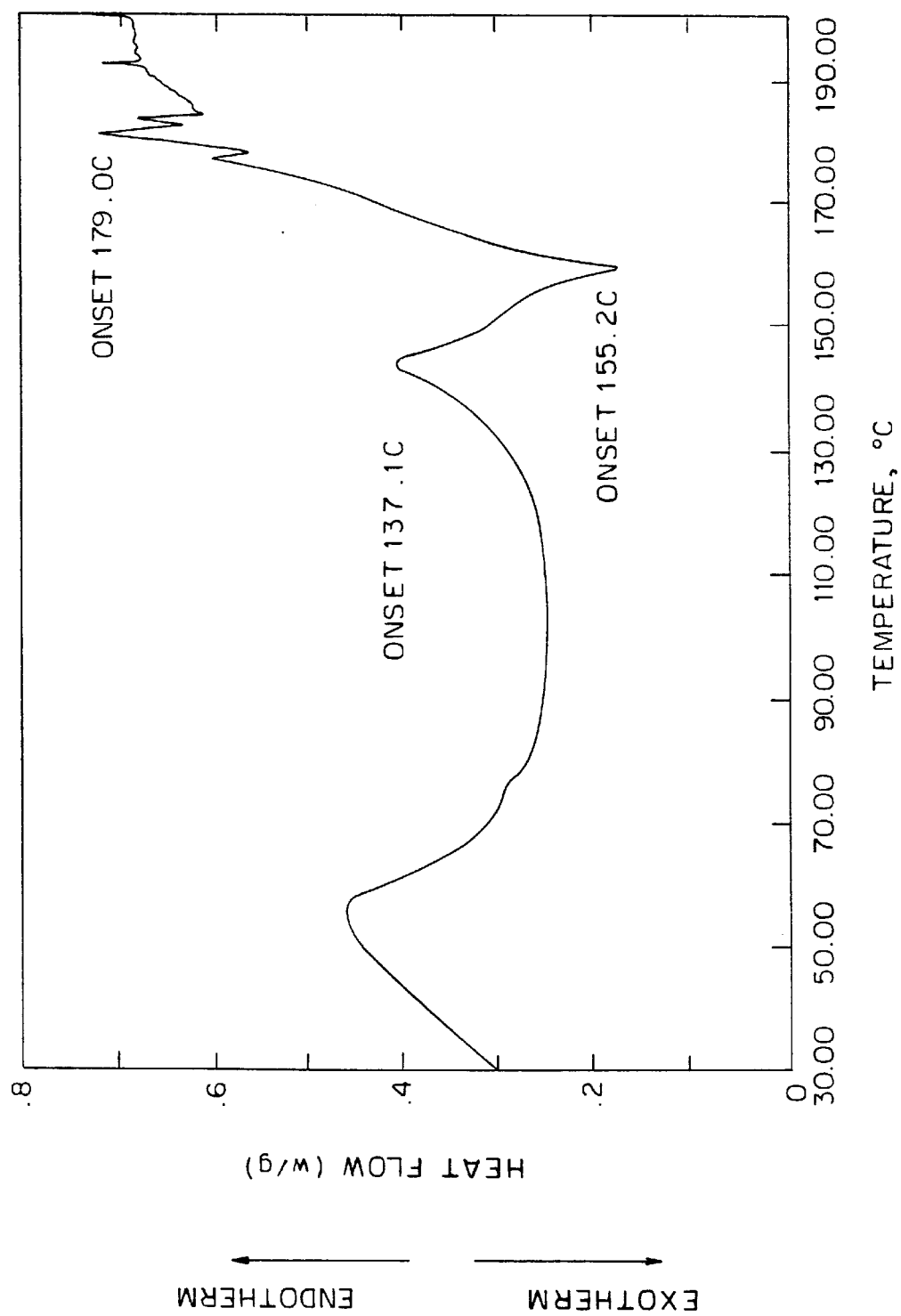
FIG. 5 shows a DSC curve obtained by thermal analysis of crystal form C.
Figure 6:
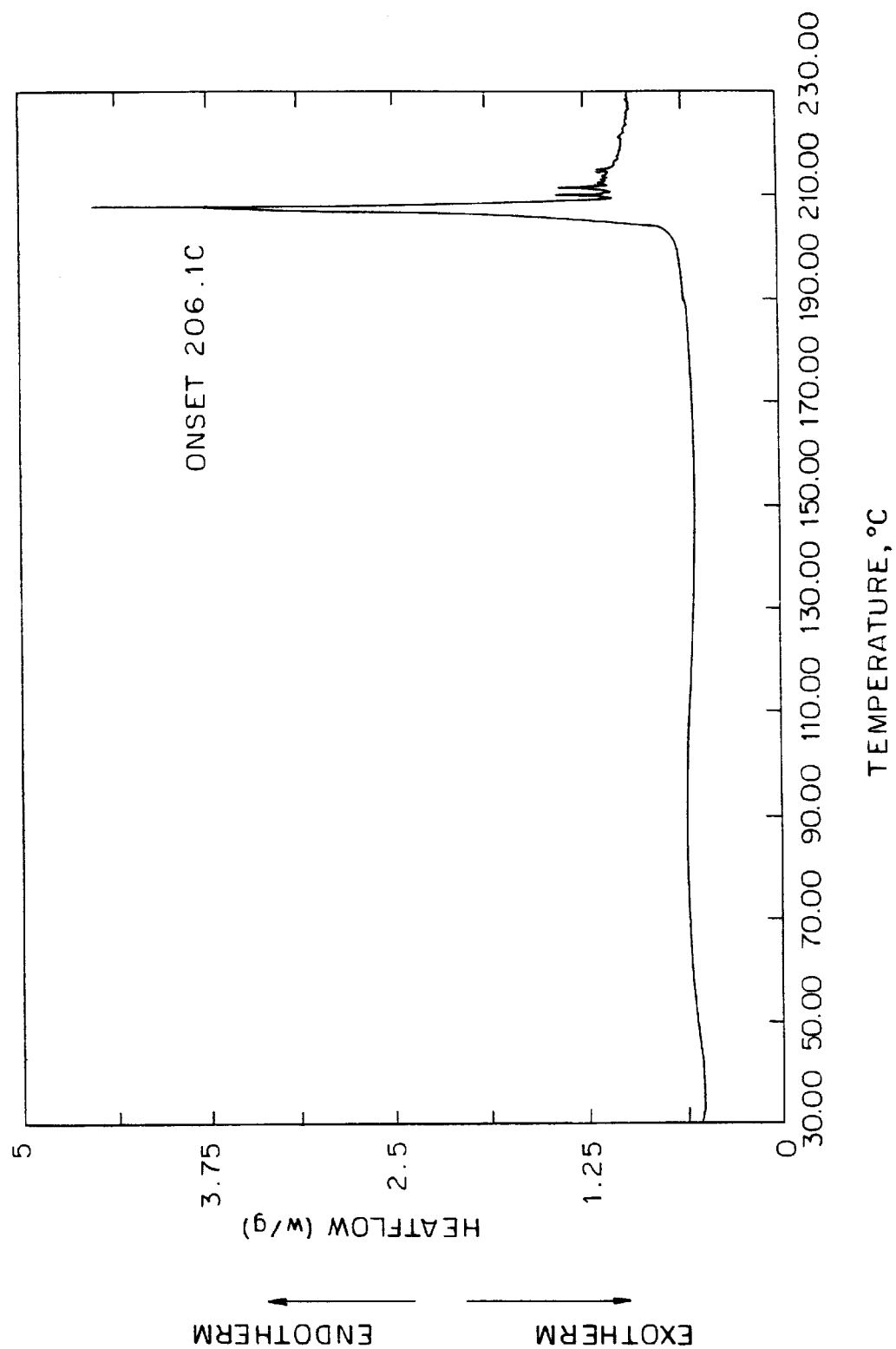
FIG. 6 shows a DSC curve obtained by thermal analysis of crystal form D.

The term "lower alkyl group" as used herein covers straight or branched-chain alkyl groups having 1–6 carbon atoms and specific examples include a methyl, ethyl, n-propyl, isopropyl, n-butyl, isobutyl, sec-butyl, tert-butyl, pentyl and a hexyl group, with methyl, ethyl, n-propyl and isopropyl groups being preferred. A particularly preferred example of $R_1$ is an isopropyl group and a particularly preferred example of $R_2$ is a methyl group.

Examples of the production process of the invention are shown below schematically (Reaction Path 1).

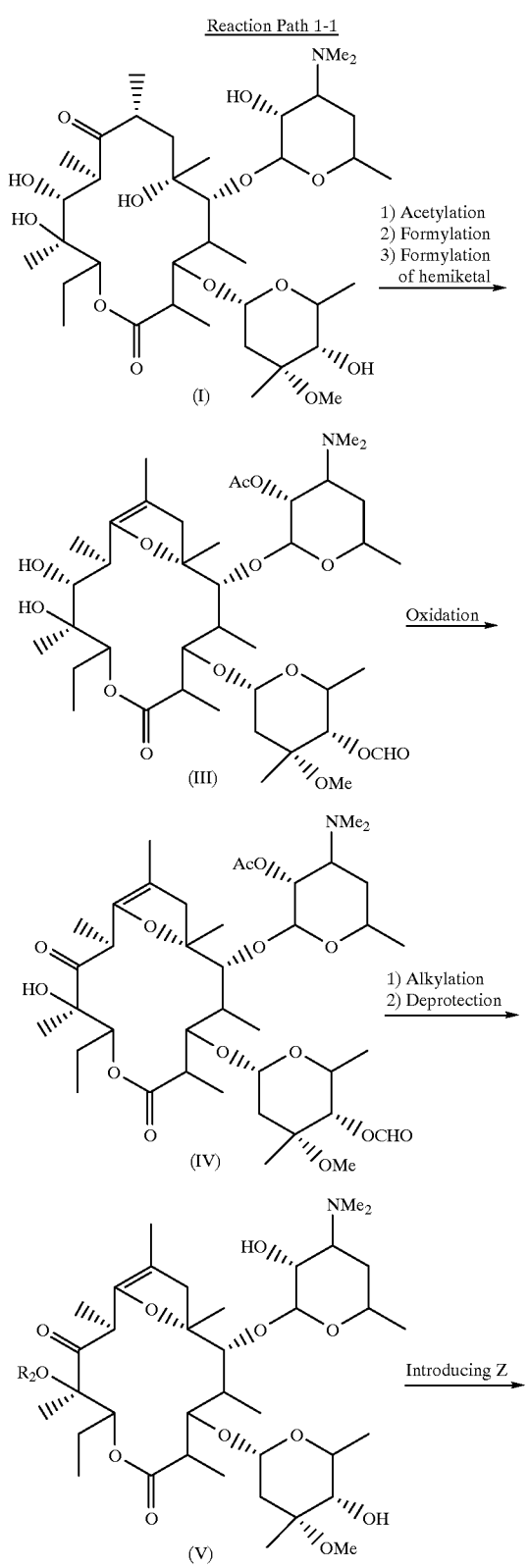
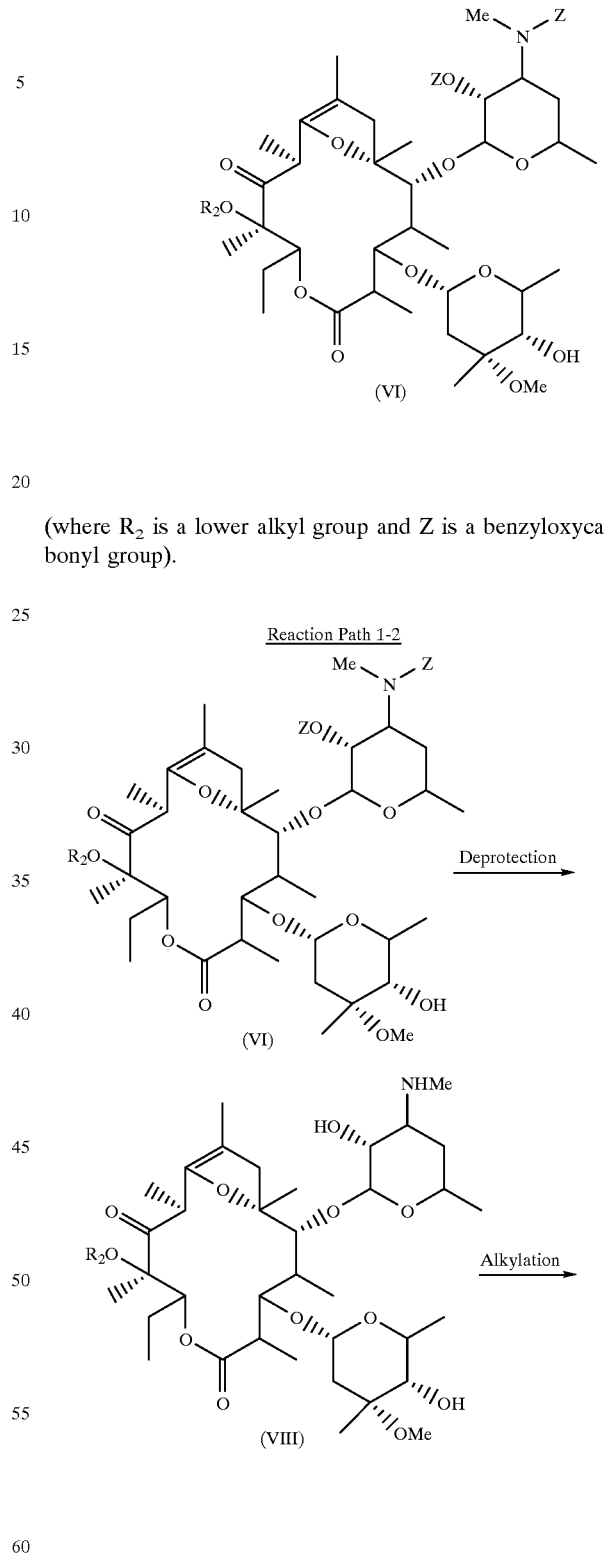
(where $R_2$ is a lower alkyl group and Z is a benzyloxycarbonyl group).

-continued

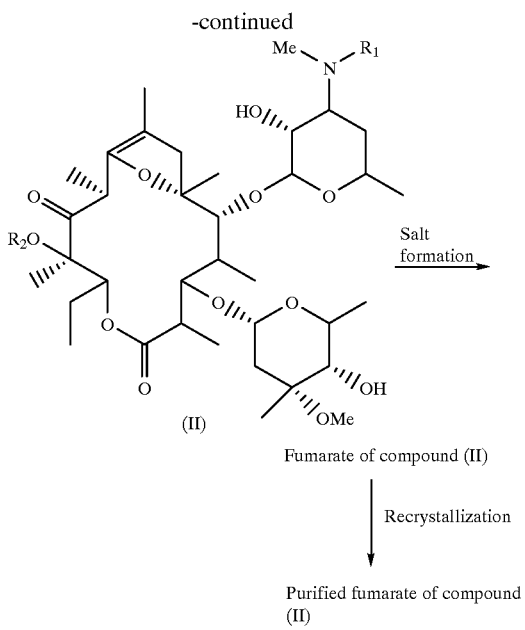

(II)

Fumarate of compound (II)

↓ Recrystallization

Purified fumarate of compound (II)

(where R₁ is a lower alkyl group, R₂ is a lower alkyl group, and Z is a benzyloxycarbonyl group).

Thus, the hydroxyl group in position 2' of erythromycin [compound of the formula (I)] is acetylated in the presence of a base and thereafter the hydroxyl group in position 4" is formylated and then subjected to a reaction for the formation of hemiketal, thereby yielding a compound of the formula (III). The three stages of reaction, i.e., acetylation, formylation and the formation of hemiketal, are preferably carried out in one pot.

Examples of the base for use in acetylation which is the first-stage reaction include inorganic bases and organic bases such as amines; preferred examples are organic bases such as pyridine, triethylamine, diisopropylethylamine, pyrrolidine, piperidine, morpholine, diethylamine and diisopropylamine, with pyridine being more preferred. Solvents preferred for use are those which are inert to the three stages of reaction, i.e., acetylation, formulation and the formation of hemiketal, and they may be exemplified by ethyl acetate, acetone, dichloromethane and chloroform, with ethyl acetate and acetone being more preferred, among which ethyl acetate is the most preferred. Examples of acetylating agent include acetic anhydride, acetyl chloride and sodium acetate, with acetic anhydride and acetyl chloride being preferred, among which acetic anhydride is the most preferred. The reaction temperature ranges preferably from about 0° C. to about 50° C., with room temperature and whereabouts being more preferred. The reaction time ranges generally from about 30 minutes to 3 hours, preferably from 1 hour to 2 hours.

Preferred examples of the formylating agent for use in formylation which is the second-stage reaction include formic acid-acetic anhydride and sodium formate-acetyl chloride, with formic acid-acetic anhydride being more preferred. Examples of the base that can be used include inorganic bases and organic bases such as amines, with pyridine, triethylamine, diisopropylethylamine, pyrrolidine, piperidine, morpholine, diethylamine and diisopropylamine, among which pyridine is more preferred. It should, however, be noted that if the acetylation and formylation reactions are to be carried out successively, the base used in the first reaction may serve for the second reaction, thus eliminating the need to employ an additional base. The reaction temperature for formylation ranges preferably from about −40° C. to about 5° C., more preferably from −20° C. to 0° C. The reaction time ranges generally from about 1 hour to about 1 day, preferably from about 5 hours to about 12 hours.

Formation of hemiketal which is the third-stage reaction is carried out under acidic conditions. The term "acidic conditions" means the presence of an acid in the reaction system. The acid may be an organic acid, which is preferably a carboxylic acid such as acetic acid or formic acid, with acetic acid being more preferred. If the first-through the third-stage reaction is to be carried out in one pot, the acetic acid or formic acid is brought into the system from the preceding stage of reaction and, hence, the intended reaction will proceed without adding an acid in the third stage. The temperature for the third-stage reaction ranges preferably from about room temperature to about 60° C., more preferably from 40° C. to 50° C. The reaction time ranges generally from about 1 hour to about 1 day, preferably from about 2 hours to about 12 hours.

The resulting compound of the formula (III) is subjected to an oxidation reaction so as to oxidize the hydroxyl group in position 11. Exemplary oxidizing agents include organic oxidants such as dimethyl sulfoxide and Dess-Martin Periodinane reagent and metal oxides such as ruthenium tetroxide and preferred examples include dimethyl sulfoxide-dicyclohexylcarbodiimide and dimethyl sulfoxide-trifluoroacetic anhydride, with dimethyl sulfoxide-trifluoroacetic anhydride being particularly preferred. Any solvents that are inert to the reaction may be employed; if dimethyl sulfoxide-trifluoroacetic anhydride is used as the oxidant, halogen-containing solvents such as chloroform and dichloromethane are preferably used as solvents, with dichloromethane being more preferred. The temperature for the oxidation reaction ranges preferably from about −60° C. to about 0° C., more preferably from about −20° C. to about −10° C. The reaction time ranges generally from about 30 minutes to about 5 hours, preferably from 1 hour to 2 hours.

The resulting compound of the formula (IV) is reacted with an alkylating agent under basic conditions to alkylate the hydroxyl group in position 12. Subsequently, the protective groups in positions 2' and 4" are removed. In this case, the alkylation and the reaction for removing the protective groups are preferably carried out in one pot.

Examples of the alkylating agent for use in alkylation which is the first-stage reaction are alkyl halides, alkyl tosylates and alkyl imidates, with alkyl tosylates and alkyl halides being preferred. A methyl group is particularly preferred as the alkyl portion of these alkylating agents. Specific examples of the methylating agent include methyl iodide and methyl tosylate, with methyl tosylate being preferred. Exemplary bases that can be used include metal hydrides, metal hydroxides and metal alkoxides and metal hydrides are preferred, with sodium hydride being particularly preferred. Any solvents that are inert to the reaction may be used but aprotic polar solvents are preferred, with dimethylimidazolidinone, dimethylformamide, dimethyl acetamide, tetrahydrofuran and acetonitrile being more preferred, among which dimethylimidazolidinone and dimethylformamide are particularly preferred. The reaction temperature ranges preferably from about 0° C. to about 60° C., more preferably from 0° C. to 30° C. The reaction time ranges generally from about 1 hour to about 12 hours, preferably from 2 hours to 8 hours.

The removal of protective groups which is the second-stage reaction is carried out by ordinary methods of carrying out the reaction for removing acetyl and formyl groups, preferably under basic conditions. Exemplary bases that can be used include inorganic bases such as sodium hydrogencarbonate and potassium carbonate, with sodium hydrogencarbonate being more preferred. Any solvents that are inert to the reaction may be used but alcoholic solvents are preferred, with methanol and ethanol being more preferred. The reaction temperature ranges preferably from about 40° C. to about 80° C., more preferably from 50° C. to 60° C. The reaction time ranges generally from about 1 hour to about 12 hours, preferably from 3 hours to 8 hours.

If the alkylation and deprotection reactions are to be carried out in one pot, alkylation which is the first-stage reaction may be performed using a base in excess amount, say, 2 equivalent amounts or more, preferably about 2 equivalent amounts; the resulting basicity of the base eliminates the need to use an additional base in the second-stage reaction. If desired, solvents may optionally be exchanged in each stage by, for example, supplementing the solvent for the first-stage reaction with the solvent for the second-stage reaction.

The thus produced compound of the general formula (V) is reaction with an excess amount of benzyloxycarbonyl chloride under basic conditions so that said compound is converted to a compound of the general formula (VI); thereafter, the introduced benzyloxycarbonyl group is removed by the usual method, whereby the compound of the general formula (VI) is converted to a compound of the general formula (VIII) which, in turn, is reacted with an alkylating agent under basic conditions so that it is converted to a compound of the general formula (II), which is treated by the usual method for conversion to a fumarate. The series of reactions consisting of benzyloxycarbonylation, de-benzyloxycarbonylation, alkylation and conversion to a fumarate can be carried out to the final stage, i.e., the formation of a fumarate of the compound of the general formula (II), without purifying the products obtained at the respective stages.

A preferred example of the benzyloxycarbonylating agent for use in the first stage is benzyloxycarbonyl chloride. Examples of the base that can be used include inorganic bases such as sodium hydrogencarbonate and potassium carbonate, with sodium hydrogencarbonate being preferred. Any solvents that are inert to the reaction may be employed but aromatic hydrocarbon-based solvents are preferred, with toluene, etc. being more preferred. The reaction temperature ranges preferably from about 30° C. to about 80° C., more preferably from 45° C. to 70° C., with 60° C. and whereabouts being particularly preferred. The reaction time ranges generally from about 2 hours to about 12 hours, preferably from 4 hours to 8 hours. It should be noted that the benzyloxycarbonylating agent must be used in an excess amount over the compound of the general formula (V), preferably in 9–15 equivalent amounts, more preferably in 10–12 equivalent amounts.

Removal of the benzyloxycarbonyl group which is the second-stage reaction is carried out by an ordinary method of deprotection. An exemplary method of deprotection is catalytic hydrogenation, preferably using a palladium-carbon catalyst. The source of hydrogen is typically hydrogen but ammonium formate may also be employed. If hydrogen is used as the source of hydrogen, catalytic hydrogenation may be performed under superatomospheric pressure, which ranges preferably from about 2 to 5 atmospheres, more preferably from 3 to 4 atmospheres. Any solvents that are inert to the reaction may be employed but alcoholic solvents and the like are preferred, with methanol, ethanol, etc. being more preferred. The reaction temperature ranges from about 0° C. to about 50° C., preferably from about 10° C. to about 30° C., with room temperature and whereabouts being more preferred. The reaction time ranges from about 30 minutes to about 3 hours, preferably from 1 hour to 2 hours. If ammonium formate is used as the source of hydrogen, any solvents that are inert to the reaction may be employed but alcoholic solvents and the like are preferred, with methanol, ethanol, etc. being more preferred. The reaction temperature ranges preferably from about 50° C. to about 100° C., more preferably from 60° C. to about 90° C. The reaction time ranges generally from about 30 minutes to about 3 hours, preferably from 1 hour to 2 hours.

Examples of the alkylating agent for use in alkylation which is the third-stage reaction include alkyl halides and alkyl tosylates, with alkyl halides being preferred. An isopropyl group is particularly preferred as the alkyl portion of these alkylating agents. Preferred examples of the isopropylating agent include isopropyl iodide. Exemplary bases that can be used include organic bases such as amines, as well as inorganic bases; preferred examples include diisopropyletylamine, triethylamine, morpholine, piperidine, pyrrolidine and pyridine, with triethylamine being particularly preferred. Any solvents that are inert to the reaction may be employed but aprotic polar solvents, alcoholic solvents and the like are preferred, with dimethylimidazolidinone, dimethylformamide, dimethyl acetamide, acetonitrile, tetrahydrofuran, methanol, ethanol, etc. being more preferred, among which dimethylimidazolidinone, dimethylformamide and acetonitrile are particularly preferred. The reaction temperature ranges preferably from about 50° C. to about 100° C., more preferably from 60° C. to 80° C. The reaction time ranges generally from about 3 hours to about 10 days, preferably from 5 hours to 10 hours.

Conversion to a fumarate which is the fourth-stage reaction is carried out by an ordinary salt forming method. Solvents preferred for use are alcoholic solvents, ether-based solvents such as tetrahydrofuran, acetone, etc., with methanol, ethanol, isopropanol, etc. being more preferred. The reaction temperature ranges preferably from about −20° C. to about 50° C., more preferably from about −15° C. to about room temperature. The reaction time ranges generally from about 1 hour to 6 hours, preferably from 3 hours to 4 hours.

The thus obtained fumarate of the compound of the general formula (II) is purified as required. Recrystallization is a preferred purification technique. Exemplary solvents for recrystallization include optionally water-containing ester-based solvents, alcoholic solvents, ether-based solvents and mixtures thereof and preferred examples are ethanol, a mixture of methanol and isopropanol, and a mixture of ethyl acetate and water; among these solvents, a mixture of methanol and isopropanol, a mixture of ethyl acetate and water, etc. are more preferred. In these mixed solvent systems, the methanol to isopropanol ratio may range from about 10:90 to about 50:50, preferably from about 20:80 to about 30:70, and the ethyl acetate to water ratio may range from 99.5:0.5 to 97:3, preferably from 99:1 to 98:2, with a value of about 98.5:1.5 being more preferred.

When recrystallization was performed with ethyl acetate used as a solvent either alone or in admixture with water, there were obtained crystals (crystal forms C and D) that differed from the product (crystal form A) of recrystallization from a mixture of methanol and isopropanol which is described in Japanese Patent Public Disclosure No. 56873/1994. The data on powder X-ray diffraction and thermal analysis (DSC) of these crystals are shown in the accompanying figures (FIGS. 1–6).

In the crystal (crystal form A) which was obtained by recrystallization from the mixture of methanol and isopropanol, the molar ratio of the compound of the formula (VII) to fumaric acid was 2:1. The crystal obtained by recrystallization with ethyl acetate used as a solvent either alone or in admixture with water was either of form C in which the molar ratio of the compound of the formula (VII) to fumaric acid was 1:1 or of form D in which the stated molar ratio was 2:1.

Among these crystal forms, the crystal of form D which was obtained by recrystallizing with a mixture of ethyl acetate and water the fumarate (e.g., crystal form A) of the compound of the formula (VII) which was partially purified by, for example, recrystallization from a mixture of methanol and isopropanol was found to have better quality such as higher stability than the other forms of crystal in terms of use as a pharmaceutical or a starting material therefor.

In order to obtain the crystal form D, recrystallization with the mixture of ethyl acetate and water is preferably performed in the following manner: first, the partially purified fumarate of the compound of the formula (VII) is suspended or dissolved in ethyl acetate at a temperature near room temperature and, after addition of water, the suspension or solution is cooled to a temperature of from about $-10°$ C. to about $-20°$ C.

The following examples are provided for the purpose of further illustrating the present invention but are in no way to be taken as limiting. In the following description, only characteristic peaks are noted in the $^1$H-NMR spectral data.

EXAMPLE 1
Synthesis of Hemiketal form [Compound of the Formula (III)]

Erythromycin A (20.0 g, 0.027 mol) were dissolved in acetic anhydride (3.34 g, 0.033 mol), pyridine (3.45 g, 0.044 mol) and ethyl acetate (80 ml) and the solution was stirred at room temperature for 1 hour. Thereafter, formic acid (11.29 g, 0.245 mol) and acetic anhydride (12.52 g, 0.123 mol) were added dropwise to the solution under cooling with ice ($0°$ C.) and the mixture was stirred for 3 hours on ice cooling. Thereafter, the mixture was gradually reverted to room temperature and left to stand overnight.

The mixture was heated at $40-50°$ C. for about 2 hours. After the mixture was reverted to room temperature, it was dissolved in ethyl acetate (120 ml) and the solution was washed with ice water (60 ml×2). The ethyl acetate layer was neutralized with a saturated aqueous solution of sodium hydrogencarbonate (120 ml) and solid sodium hydrogencarbonate (8 g or more). The ethyl acetate layer was separated, washed with water (40 ml×3) and saturated brine (40 ml), and dried with anhydrous sodium sulfate overnight.

Following filtration concentrating was effected under vacuum. The residue was refluxed with hexane (136 ml) for about 30 minutes and thereafter cooled. Following the addition of ethyl acetate (24 ml), cooling to $0°$ C. was effected under stirring. The resulting crystal was separated and washed with hexane (20 ml) to yield the titled compound (15.8 g, 74%) as a white crystal.

m.p.: $200-208°$ C. (ethyl acetate-hexane); $^1$H-NMR (CDCl$_3$): 0.89(3H,t,13—CH$_2$C$\underline{H}_3$), 2.05(3H,s,2'—OCOC$\underline{H}_3$), 2.27(6H,s,3'—N(C$\underline{H}_3$)$_2$), 3.36(3H,s,3"—OC$\underline{H}_3$), 3.83 (1H,s,11—C$\underline{H}$(OH)), 8.20(1H,s,4"—OC$\underline{H}$O).

EXAMPLE 2
Synthesis of Oxo form [Compound of the Formula (IV)]

A portion (10.0 g, 0.013 mol) of the compound prepared in Example 1 and dimethyl sulfoxide (2.64 g, 0.032 mol) were dissolved in dichloromethane (50 ml). The reaction system was cooled to $-20°$ C. with ice-sodium chloride and trifluoroacetic anhydride (3.36 g, 0.016 mol) was added dropwise at $-10°$ C. or below to the reaction mixture, which was stirred for 20 minutes. Further, with the reaction system held at $-20°$ C., triethylamine (3.49 g, 0.034 mol) was added dropwise at $-10°$ C. or below and stirring was continued for 20 minutes. Following the addition of a saturated aqueous solution of sodium hydrogencarbonate (50 ml), the mixture was stirred for 20 minutes. Washing with water (50 ml×3) was followed by drying with anhydrous sodium sulfate overnight.

After the dichlormethane was concentrated under vacuum, hexane (100 ml) was added to the syrupy residue, which was stirred while hot to form a solution. After the solution was cooled, dichloromethane (2.5 ml) was added and the mixture was stirred at room temperature for 2.5 hours. The crystal was recovered by filtration and washed with 2.5% dichloromethane-hexane (30 ml) to yield the titled compound (6.49 g, 65%) as a white crystal.

m.p.: $186-188°$ C. (dichloromethane-hexane); $^1$H-NMR (CDCl$_3$): 0.90(3H,t,13—CH$_2$C$\underline{H}_3$), 2.04(3H,s,2'—OCOC$\underline{H}_3$), 2.26(6H,s,3'—N(C$\underline{H}_3$)$_2$), 3.33(3H,s,3"—OC$\underline{H}_3$), 4.53 (1H,d,1'—H), 4.84(1H,d,1"—H), 4.97(1H,dd,13—H), 8.21 (1H,s,4"-OC$\underline{H}$O). $^{13}$C-NMR(CDCl$_3$): 208.4(11—$\underline{C}$O).

EXAMPLE 3
Synthesis of Deprotected form [Compound of the Formula (V) (R$_2$: Methyl)]

To dimethylformamide (30 ml), there was added 60% sodium hydride (1.02 g, 0.026 mol); to the mixture, compound (10.0 g, 0.013 mol) prepared in Example 2 was added and the resulting mixture was stirred for 30 minutes. After methyl tosylate (2.38 g, 0.013 mol) was added dropwise, the mixture was stirred first at $0-5°$ C. for 1 hour, then at $15-20°$ C. for 1.5 hours. After addition of methanol (60 ml), the mixture was heated at $60°$ C. for 5 hours. The as-heated mixture was left to stand overnight.

The whole mixture was concentrated under vacuum and the concentrate was added dropwise to warm water (150 ml) at $40°$ C. under stirring for precipitate separation. The stirring was further continued for 30 minutes in warm water (150 ml) at $40°$ C. for precipitate separation. The precipitate was dried at $50°$ C. for 4 hours to yield a crude deprotected form (7.9 g, 85%).

The crude deprotected form was dissolved in acetone (12.6 ml) and 10% aqueous ammonia (5.9 ml) was added for crystallization. For phase separation and washing, the mixture was stirred first at $15-25°$ C. for 1 hour, then, at $-5$ to $-10°$ C. for 1 hour. Upon drying at $50°$ C. for 3 hours, the titled compound (5.5 g, 59%) was yielded as a pale yellow crystal.

m.p.: $168-174°$ C. (aqueous ammonia-acetone); $^1$H-NMR (CDCl$_3$): 0.85(3H,t,13—CH$_2$C$\underline{H}_3$), 1.68(3H,s,8—C$\underline{H}_3$), 2.28(6H,s,3'—N(C$\underline{H}_3$)$_2$), 3.06(3H,s,12—OC$\underline{H}_3$), 3.34(3H,s, 3"—OC$\underline{H}_3$), 4.37(1H,d,1'—H), 4.97(1H,d,1"—H), 5.63(1H, dd,13—H).

EXAMPLE 4
Synthesis of Benzyloxycarbonyl form [Compound of the Formula (VI) (R$_2$: Methyl)]

To toluene (55 ml), there were added the compound (5.5 g, 0.0076 mol) prepared in Example 3 and solid sodium hydrogencarbonate (9.5 g, 0.113 mol). Subsequently, benzyloxycarbonyl chloride (18.0 g, 0.106 mol) was added dropwise at $70-80°$ C. under stirring and the mixture was heated at the same temperature for 4 hours. The liquid reaction mixture was then left to stand overnight at room temperature.

Pyridine (4.02 g, 0.05 mol) was added to the liquid reaction mixture, which was stirred for 30 minutes. Subsequently, a saturated aqueous solution of sodium hydrogencarbonate (38.5 ml) was added and the mixture was stirred for 10 minutes, followed by the addition of ethyl acetate (38.5 ml). The mixture was stirred for phase separation and the resulting organic layer was washed with water. The organic layer was further washed with saturated brine (38.5 ml) and dried with anhydrous sodium sulfate.

The whole mixture was concentrated under vacuum. Acetonitrile (27.5 ml) was added to the residue and the resulting solution was washed with hexane (187 ml×5) for phase separation. The acetonitrile layer was concentrated under vacuum. Methanol (13.5 ml) was added to the residue and the mixture was stirred first at 15–25° C. for 1 hour, then at 0° C. or below for 1 hour. The precipitating crystal was recovered by filtration and dried at 50° C. for 3 hours to yield the titled compound (4.0 g, 54%) as a white crystal.

m.p.: 122–126° C. (methanol) $^1$H-NMR (CDCl$_3$): 0.96 (3H,t,13—CH$_2$C$\underline{H}_3$), 1.68(3H,s,8—C$\underline{H}_3$), 3.03–3.37(3H,d,3"—OC$\underline{H}_3$), 3.06(3H,s,12—OC$\underline{H}_3$), 5.03–5.21(4H,m,C$\underline{H}_2$C$_6$H$_5$×2), 5.63(1H,dd,13—H), 7.28–7.34(10H,m,2'—OCOCH$_2$C$_6$$\underline{H}_5$, 3'—NOCOCH$_2$C$_6$$\underline{H}$5).

EXAMPLE 5
Synthesis of De-Benzyloxycarbonylated form [Compound of the Formula (VIII) (R$_2$: Methyl)]

To methanol (36.8 ml), there were added the compound (4.0 g, 0.004 mol) prepared in Example 4, 10% palladium-carbon (0.4 g) and ammonium formate (1.03 g) and the mixture was heated under reflux for 1 hour. The palladium-carbon as filtered off and the methanol was then distilled off under vacuum. The residue was dissolved in ethyl acetate (40 ml) and the solution was washed with a saturated aqueous solution of sodium hydrogencarbonate (16 ml) for phase separation. The resulting organic layer was washed first with water (16 ml×2), then with saturated brine (16 ml) and dried with anhydrous sodium sulfate. After the anhydrous sodium sulfate was filtered off, the organic layer was concentrated under vacuum to yield a crude de-benzyloxycarbonylated form (2.0 g, 69%) as s white crystal.

m.p.: 187–190° C. (as suspended in hexane for purification); $^1$H-NMR (CDCl$_3$): 0.95(3H,t,13—CH$_2$C$\underline{H}_3$), 1.68(3H,s,8—C$\underline{H}_3$), 2.47(3H,s,3'—NHC$\underline{H}_3$), 3.06(3H,s,12—OC$\underline{H}_3$), 3.21(1H,dd,2"—H), 3.33(3H,s,3"—OC$\underline{H}_3$), 4.37(1H,d,1'—H), 4.96(1H,d,1"—H), 5.61–5.65(1H,dd,13-H).

EXAMPLE 6
Synthesis of Fumarate form [Fumarate of the Compound of the Formula (VII)]

To dimethylimidazolidinone (35 ml), there were added the compound (10 g, 0.014 mol) prepared in Example 5, isopropyl iodide (23.8 g, 0.14 mol) and triethylamine (16.95 g, 0.17 mol) to form a solution, which was heated at 70–75° C. for 7–8 hours and left to stand overnight. After extraction and washing with ethyl acetate (200 ml) and 2.5% aqueous ammonia (75 ml), the solution was washed with water (150 ml×2), then with saturated brine (100 ml) and dried with anhydrous sodium sulfate. After the ethyl acetate was concentrated under vacuum, the residue and fumaric acid (0.84 g, 0.0073 mol) were dissolved in methanol (25 ml). Under stirring, isopropanol (75 ml) was slowly added dropwise to the solution to yield a fumarate form. The liquid reaction mixture containing the fumarate form was stirred first at room temperature for 1 hour, then at 0° C. for 1 hour and finally at −15° C. for 1 hour, followed by filtration under vacuum to yield the titled compound (7.9 g, 69%) as a white crystal.

m.p.: 194–197° C. (methanol-isopropanol); $^1$H-NMR (CDCl$_3$+DMSO-d$_6$): 0.94(3H,t,13—CH$_2$C$\underline{H}_3$), 1.73(3H,s,8—C$\underline{H}_3$), 3.05(3H,s,12—OC$\underline{H}_3$), 3.08(1H,dd,4"—H), 3.35 (3H,s,8"—OC$\underline{H}_3$), 4.43(1H,d,1'—H), 4.96(1H,d,1"—H), 5.60–5.63(1H,dd,13—H), 6.78(1H,s,½(=C$\underline{H}$—COOH)$_2$).

EXAMPLE 7
Partial Purification of the Fumarate form [Fumarate of the Compound of the Formula (VII)]

The compound (10.0 g, 0.0123 mol) prepared in Example 6 was dissolved in methanol (25 ml) and isopropanol (75 ml) was slowly added dropwise to the solution. The liquid reaction mixture was stirred first at room temperature for 1 hour, then at 0° C. for 1 hour and finally at −15° C. for 1 hour to accomplish crystallization. Filtration under vacuum yielded a partially purified product of the titled compound (9.25 g, 92.5%) as a white crystal.

m.p.: 194–197° C. (methanol-isopropanol); $^1$H-NMR (CDCl$_3$+DMSO-d$_6$): 0.94(3H,t,13—CH$_2$C$\underline{H}_3$), 1.73(3H,s,8—C$\underline{H}_3$), 3.05(3H,s,12—OC$\underline{H}_3$), 3.08(1H,dd,4"—H), 3.35 (3H,s,8"—OC$\underline{H}_3$), 4.43(1H,d,1'—H), 4.96(1H,d,1"—H), 5.60–5.63(1H,dd,13—H), 6.78(1H,s,½(=C$\underline{H}$—COOH)$_2$).

EXAMPLE 8
Complete Purification of the Fumarate form [Fumarate of the Compound of the Formula (VII)]

The partially purified fumarate (10 g, 0.0123 mol) obtained in Example 7 was dissolved in ethyl acetate (100 ml) at room temperature. After water (1.5 ml) was added dropwise, the solution was stirred first at room temperature for 1 hour, then at 0° C. for 1 hour and finally at −10° C. for 4 hours. Filtration under vacuum yielded a fully purified product of the titled compound (9.04 g, 90.4%) as a white crystal.

m.p.: 199–200° C. (1.5% water-ethyl acetate); $^1$H-NMR (CDCl$_3$+DMSO-d$_6$): 0.94(3H,t,13—CH$_2$C$\underline{H}_3$), 1.73(3H,s,8—C$\underline{H}_3$), 3.05(3H,s,12-OC$\underline{H}_3$), 3.08(1H,dd,4"—H), 3.35 (3H,s,8"—OC$\underline{H}_3$), 4.43(1H,d,1'—H), 4.96(1H,d,1"—H), 5.60–5.63(1H,dd,13—H), 6.78(1H,s,½(=C$\underline{H}$-COOH)$_2$).

EXAMPLE 9
Synthesis of Fumarate form [Fumarate of the Compound of the Formula (VII)

To toluene (55 ml), there were added the compound (9.5 g, 0.013 mol) obtained in Example 3 and solid sodium hydrogencarbonate (16.4 g, 0.195 mol). Under stirring, benzyloxycarbonyl chloride (31.3 g, 0.183 mol) was added dropwise at 70° C. or above and the mixture was heated at the same temperature for 4 hours and subsequently left to stand overnight at room temperature.

Pyridine (6.94 g, 0.086 mol) was added to the liquid reaction mixture, which was then stirred for 30 minutes. After a saturated aqueous solution of sodium hydrogencarbonate (66.5 ml) was added, the mixture was stirred for 10 minutes and ethyl acetate (66.5 ml) was added. The resulting liquid mixture was stirred for separating the organic layer, which was successively washed with water and saturated brine (66.5 ml) and dried with anhydrous sodium sulfate.

The whole mixture was concentrated under vacuum and the residue was dissolved in methanol (128 ml). To the solution, 10% palladium-carbon (1.28 g) was added and stirring was conducted at room temperature for 1 hour in a hydrogen atmosphere under superatmospheric pressure (3–4 atmospheres). After the palladium-carbon was filtered off, the methanol was distilled off under vacuum. The residue was dissolved in ethyl acetate (120 ml) and washed with a saturated aqueous solution of sodium hydrogen-carbonate (50 ml) for phase separation. The resulting organic layer was washed with water (50 ml×2), then with saturated brine (50 ml) and dried with anhydrous sodium sulfate. After the anhydrous sodium sulfate was filtered off, the ethyl acetate was concentrated under vacuum to yield a de-benzyloxycarbonylated form [compound of the formula (VIII) ($R_2$: methyl)] as an oil.

Without being purified, the de-benzyloxycarbonylated form was dissolved in dimethylimidazolidinone together with isopropyl iodide (20.0 g, 0.118 mol) and triethylamine (13.2 g, 0.131 mol) and the solution was heated at 70–75° C. for 7–8 hours, followed by standing overnight. After extraction and washing with ethyl acetate (100 ml) and 2.5% aqueous ammonia (50 ml), the solution was washed with water (50 ml×2) and saturated brine (50 ml) and then dried with anhydrous sodium sulfate. After the ethyl acetate was concentrated under vacuum, the residue and fumaric acid (0.76 g, 0.0066 mol) were dissolved in methanol (25.0 ml) and isopropanol (75.0 ml) was slowly added dropwise under stirring for crystallization. The solution was stirred first at room temperature for 1 hour, then at 0° C. for 1 hour and finally at −15° C. for 1 hour. Subsequent filtration under vacuum and drying yielded the titled compound (6.5 g, 60.0%) as a white crystal.

m.p.: 194–197° C. (methanol-isopropanol); $^1$H-NMR ($CDCl_3$+DMSO-$d_6$): 0.94(3H,t,13—$CH_2C\underline{H}_3$), 1.73(3H,s, 8—$C\underline{H}_3$), 3.05(3H,s,12—$OC\underline{H}_3$), 3.08(1H,dd,4"—H), 3.35 (3H,s,8"—$OC\underline{H}_3$), 4.43(1H,d,1'—H), 4.96(1H,d,1"—H), 5.60–5.63(1H,dd,13-H), 6.78(1H,s,½(=$C\underline{H}$—COOH)$_2$).

EXAMPLE 10

Stability Test with Fumarate Crystals of the Compound of the Formula (VII)

Fumarate crystals of the compound of the formula (VII) were tested for their stability which would depend on the crystal form. The crystals under test were the crystal form A which was prepared by recrystallizing the fumarate of the compound of the formula (VII) from methanol-isopropanol, as well as the crystal forms C and D which were prepared by recrystallization from ethyl acetate used as a solvent either alone or in admixture with water.

Each of the crystals was weighed precisely and subjected to an accelerated test in a thermostatic chamber filled with heated air at 80° C. Samples of each crystal were taken out of the chamber at given intervals of time and the entire portion was dissolved in 50% acetonitrile to give a concentration of ca. 1 mg/ml. To 2 ml of the solution, there was added 2 ml of an internal standard solution (consisting of 100 μg of cyclohexyl parabenzoate dissolved in 2 ml of 50% acetonitrile); thereafter, the total quantity of the mixture was adjusted to 10 ml and 100 μl of it was subjected to HPLC under conditions set forth below and the percent retention of each crystal was determined from the peak area ratio of the sample and the internal standard.

Conditions for Measurement by HPLC

Apparatus used: Multi-Solvent Feed System M600 (Waters, Inc.); Multi-Functional Detector Model 490 (Waters, Inc.);

Full-Auto Sample Processor M712 (Waters, Inc.); Data Module Model 740 (Waters, Inc.); Temperature Control Module (Waters, Inc.); Column Heater Module (Waters, Inc.)

Column: YMC A-212, $C_8$ (Y.M.C. Co., Ltd)

Eluting solution: 50% acetonitrile+low-frequency reagent PIC B-5 (Waters, Inc.)

Flow rate: 1 ml/min

Detection Wavelength: 205 nm

Column temperature: 40° C.

Internal standard: cyclohexyl parabenzoate

Figure 7:
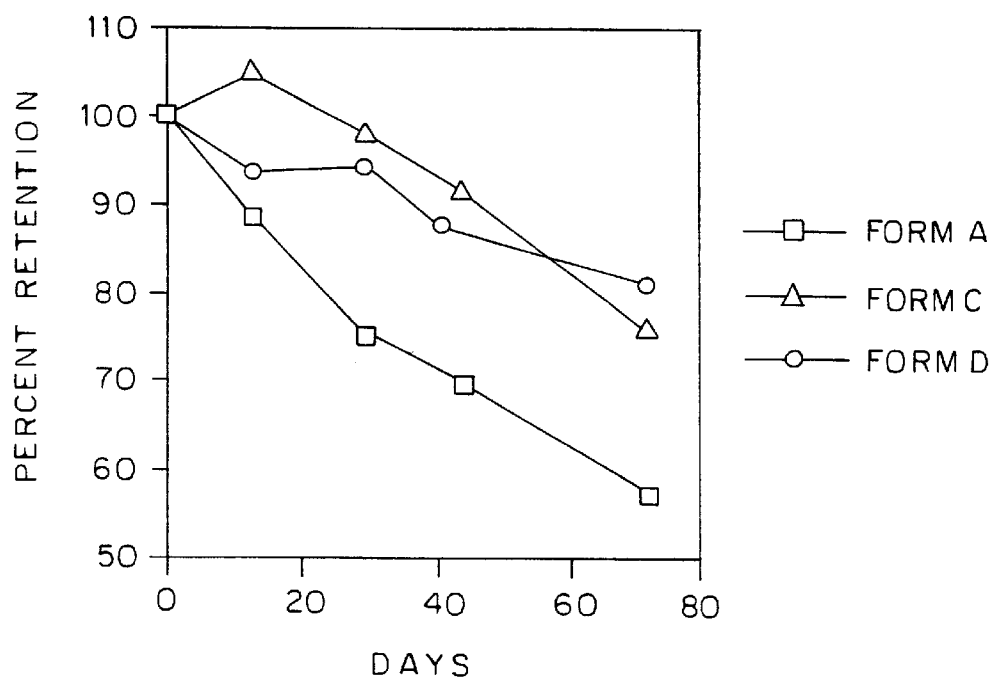
FIG. 7 is a graph showing the percent retentions of crystal forms A, C and D in a heat stability test.

The results are shown in FIG. 7. Under the test conditions, the retention of the crystal form A dropped to about 60% on the 70th day, whereas the retention of the crystal forms C and D was about 80% even on the 70th day.

EXAMPLE 11

Stability test with Fumarate Crystals of the Compound of the Formula (VII) under Humidified Conditions Fumarate crystals of the compound of the formula (VII) were tested for their stability under humidified conditions which would depend on the crystal form. The test method and conditions were the same as in Example 10, except that an accelerated test was carried out in a desiccator at 80° C. which was conditioned to a relative humidity of 75% with a saturated aqueous solution of sodium chloride.

Figure 8:
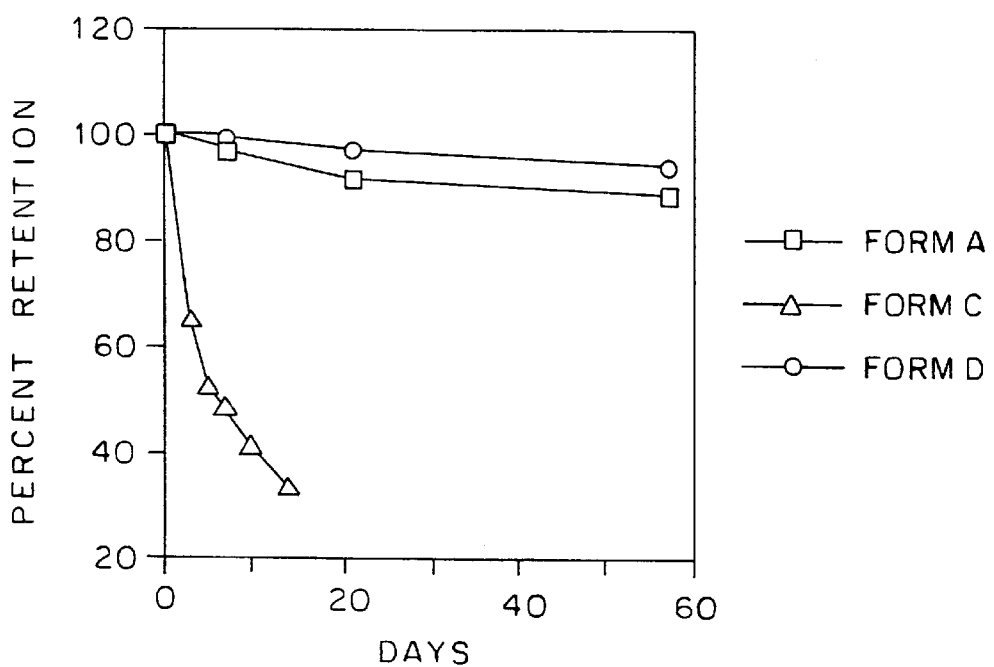
FIG. 8 is a graph showing the percent retentions of crystal forms A, C and D in a moisture stability test.

The results are shown in FIG. 8, from which one can see that the crystal forms A and D were by far more stable under humid conditions than the crystal form C.

The results of the two tests described above show that the crystal form D is more stable than the other forms.

Industrial Applicability of the Invention

The process of the invention has the following advantages: (1) purification at each of the stages of reaction necessary to obtain the purified form of the final product can be accomplished merely by recrystallization; and (2) acetylation of the hydroxyl group in position 2' of erythromycin A and formylation of the hydroxyl group in position 4" and the reaction for formation of hemiketal can be carried out in one pot and, in addition, the reaction for alkylation of the hydroxyl group in position 12, as well as the reaction for removal of the acetyl group in position 2' and the formyl group in position 4" can also be carried out in one pot. Thus, the process of the invention can yield the intended product in a smaller number of steps than the prior art methods and, hence, offers substantial benefits in commercial operations.

Further, the process of the invention can yield a fumarate crystal form of the compound of the formula (VII) that has better quality such as higher stability than the heretofore obtained crystal in terms of use as a pharmaceutical or a starting material therefor.

We claim:

1. A process for producing a fumarate of a compound of the formula (II):

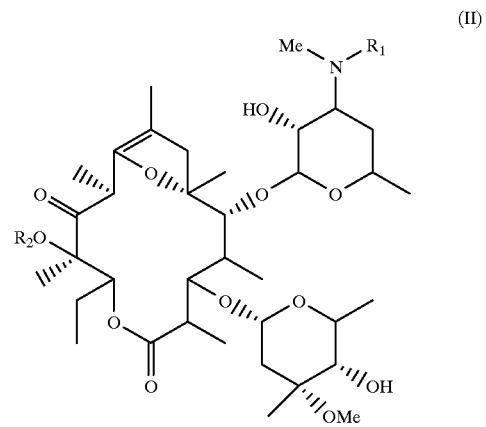

(II)

(where $R_1$ is a lower alkyl group and $R_2$ is a lower alkyl group) from erythromycin A [formula (I)]:

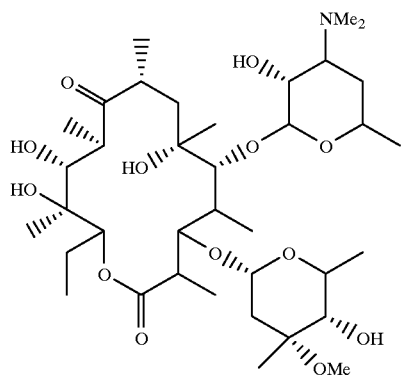
(I)

comprising the steps of acetylating the hydroxyl group in position 2' of erythromycin A, formylating the hydroxyl group in position 4" and thereafter performing a reaction for the formation of hemiketal, thereby producing a compound of the formula (III):

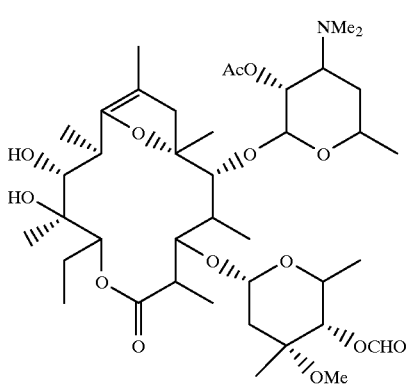
(III)

oxidizing the hydroxyl group in position 11 of the compound (III) to produce a compound of the formula (IV):

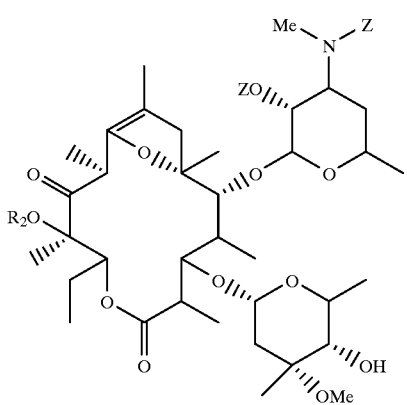
(IV)

alkylating the hydroxyl group in position 12 of the compound (IV), removing the acetyl group in position 2' and the formyl group in position 4" to produce a compound of the general formula (V):

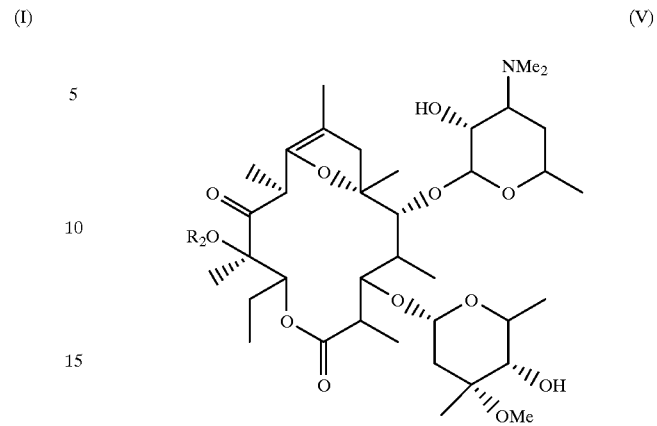
(V)

(where $R_2$ is a lower alkyl group), reacting the compound (V) with benzyloxycarbonyl chloride under basic conditions, thereafter, removing the introduced benzyloxycarbonyl group, subsequently alkylating the nitrogen atom in position 3', thereafter converting the compound to a fumarate in a crude crystal form, then recrystallizing the crude crystal from an alcoholic solvent and thereafter effecting another recrystallization from hydrous ethyl acetate.

2. A process according to claim 1, wherein the acetylation of the hydroxyl group in position 2' of erythromycin A, the formulation of the hydroxyl group in position 4" and the reaction for the formation of hemiketal are carried out in one pot.

3. A process according to claim 1, wherein the reaction for alkylating the hydroxyl group in position 12 and the reaction for removing the acetyl group in position 2' and the formyl group in position 4" are carried out in one pot.

4. A process according to claim 1, wherein the acetylation of the hydroxyl group in position 2' of erythromycin A and the formylation of the hydroxyl group in position 4" and the reaction for the formation of hemiketal are carried out in one pot and wherein the reaction for alkylating the hydroxyl group in position 12 and the reaction for removing the acetyl group in position 2' and the formyl group in position 4" are also carried out in one pot.

5. A process for producing a fumarate of a compound of the formula (II):

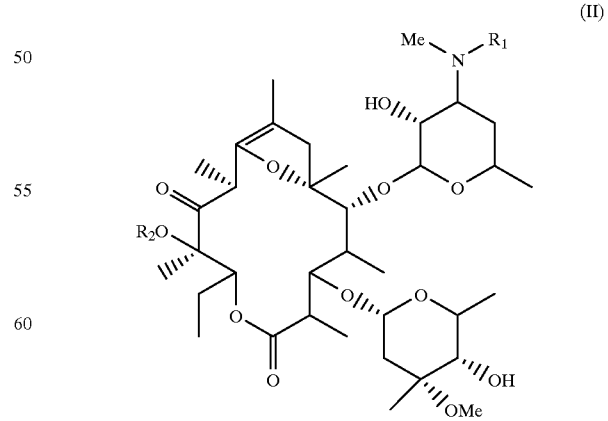
(II)

(where $R_1$ is a lower alkyl group and $R_2$ is a lower alkyl group) from erythromycin A [formula (I)]:

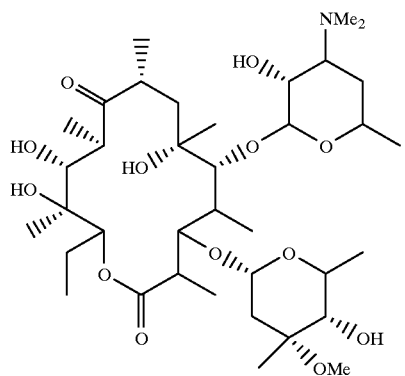
(I)

comprising the steps of acetylating the hydroxyl group in position 2' of erythromycin A, formylating the hydroxyl group in position 4" and thereafter performing a reaction for the formation of hemiketal, thereby producing a compound of the formula (III):

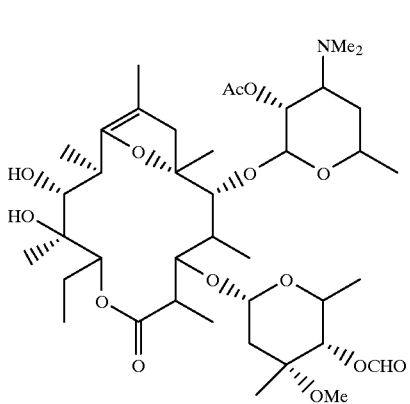
(III)

oxidizing the hydroxyl group in position 11 of the compound (III) to produce a compound of the formula (IV):

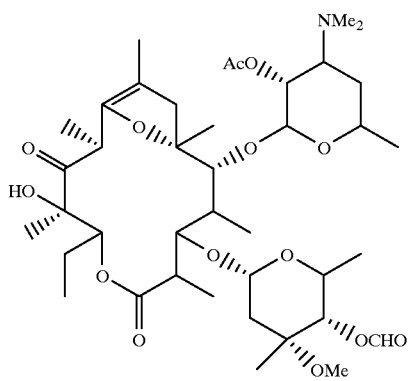
(IV)

alkylating the hydroxyl group in position 12 of the compound (IV), removing the acetyl group in position 2' and the formyl group in position 4" to produce a compound of the general formula (V):

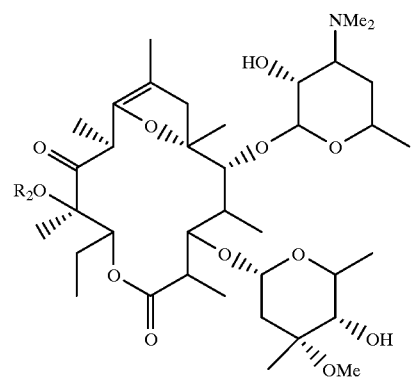
(V)

(where $R_2$ is a lower alkyl group), reacting the compound (V) with benzyloxycarbonyl chloride under basic conditions, thereafter removing the introduced benzyloxycarbonyl group, subsequently alkylating the nitrogen atom in position 3', and thereafter converting the compound to a fumarate.

6. A process according to claim 5, wherein the acetylation of the hydroxyl group in position 2' of erythromycin A, the formylation of the hydroxyl group in position 4" and the reaction for the formation of hemiketal are carried out in one pot.

7. A process according to claim 5, wherein the reaction for alkylating the hydroxyl group in position 12 and the reaction for removing the acetyl group in position 2' and the formyl group in position 4" are carried out in one pot.

8. A process according to claim 5, wherein the acetylation of the hydroxyl group in position 2' of erythromycin A and the formylation of the hydroxyl group in position 4" and the reaction for the formation of hemiketal are carried out in one pot and wherein the reaction for alkylating the hydroxyl group in position 12 and the reaction for removing the acetyl group in position 2' and the formyl group in position 4" are also carried out in one pot.

9. A process according to claim 1, wherein $R_1$ is an isopropyl group and $R_2$ is a methyl group.

10. A process for producing a compound of the formula (III):

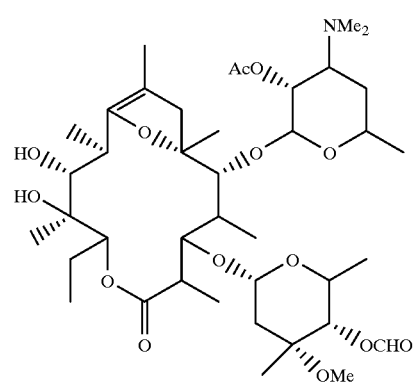
(III)

from erythromycin A of the formula (I):

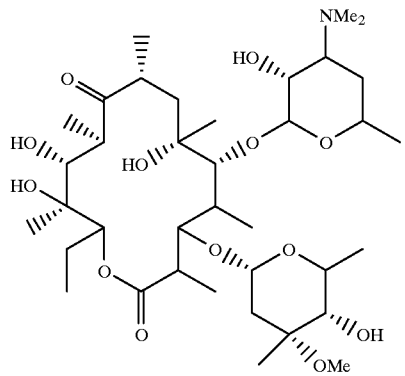
(I)

by carrying out in one pot the acetylation of the hydroxyl group in position 2' of erythromycin A, the formylation of the hydroxyl group in position 4" and a reaction for the formation of hemiketal.

11. A process for producing a compound of the formula (VI):

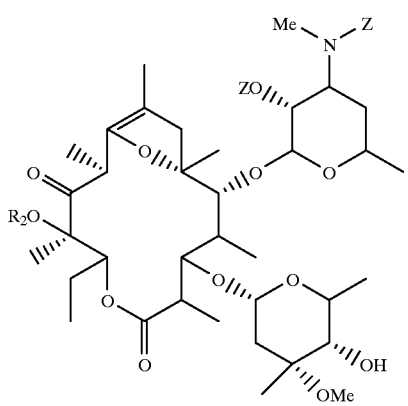
(VI)

(where $R_2$ is a lower alkyl group and Z is a benzyloxycarbonyl group) by reacting a compound of the formula (V):

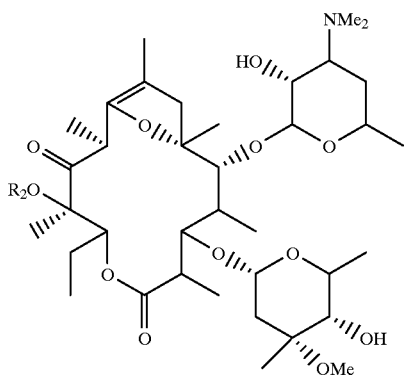
(V)

(where $R_2$ is a lower alkyl group) with benzyloxycarbonyl chloride under basic conditions.

12. A method of purifying a fumarate of a compound of the formula (II):

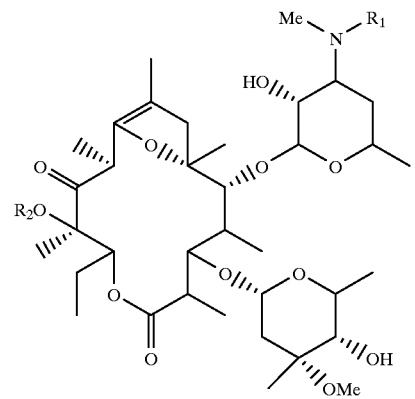
(II)

(where $R_1$ is a lower alkyl group and $R_2$ is a lower alkyl group) by recrystallizing a crude crystal of a fumarate of a compound of the formula (II):

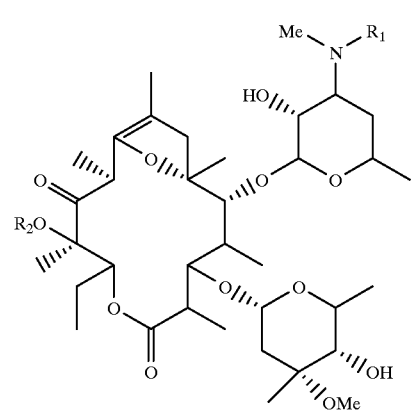
(II)

(where $R_1$ is a lower alkyl group and $R_2$ is a lower alkyl group) from an alcoholic solvent and performing another recrystallization from hydrous ethyl acetate.

13. A method according to claim 12, wherein $R_1$ is an isopropyl group and $R_2$ is a methyl group.

14. A fumarate crystal of a compound of the formula (VII):

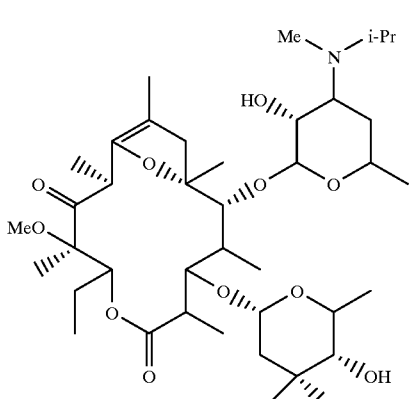
(VII)

in which the molar ratio of the compound (VII) to fumaric acid is 2:1 and which is obtained by recrystallization from hydrous ethyl acetate.

15. A process according to claim 5, wherein $R_1$ is an isopropyl group and $R_2$ is a methyl group.

* * * * *